United States Patent [19]

Yamashita

[11] Patent Number: 5,196,966
[45] Date of Patent: Mar. 23, 1993

[54] METHOD AND IMPLEMENT FOR OBSERVING OR PHOTOGRAPHING GEM SUCH AS DIAMOND

[75] Inventor: Kinsaku Yamashita, Tokyo, Japan
[73] Assignee: Masayo Yamashita, Tokyo, Japan
[21] Appl. No.: 722,536
[22] Filed: Jun. 27, 1991

[30] Foreign Application Priority Data

Jul. 6, 1990 [JP] Japan .................................. 2-177557

[51] Int. Cl.$^5$ ............................................. G02B 27/00
[52] U.S. Cl. ..................................... 359/896; 359/385; 359/798; 359/804; 359/900; 356/30; 356/240; 362/109; 362/346
[58] Field of Search ............... 359/900, 798, 800, 801, 359/802, 804, 808, 809, 810, 811, 894, 896, 601, 385, 386, 398; 356/237, 239, 240, 241, 30, 236; 362/109, 104, 260, 346

[56] References Cited

U.S. PATENT DOCUMENTS

| | | | |
|---|---|---|---|
| 3,410,634 | 11/1968 | Buckner | 359/804 |
| 3,740,142 | 6/1973 | Takubo | 356/30 |
| 3,867,032 | 2/1975 | Bruck | 356/30 |
| 3,989,379 | 11/1976 | Eickhorst | 356/30 |
| 4,152,069 | 5/1979 | Bruck | 356/30 |
| 4,461,568 | 7/1984 | Welbourn et al. | 356/30 |
| 4,906,083 | 3/1990 | Sattler | 359/386 |
| 5,045,688 | 9/1991 | Domenico et al. | 356/240 |

Primary Examiner—Loha Ben
Attorney, Agent, or Firm—Nields & Lemack

[57] ABSTRACT

There are disclosed a method and an implement for permitting one to precisely know the degree of the brilliance of a diamond, the colors of the light, and so on. A gem to be observed or photographed is placed inside a container having an opening in the top. The gem is so placed in the container that light can enter the container only from directions lying within the range of angles of 20 to 50 degrees about the line vertical to the gem. The gem inside the container is observed or photographed from above the container while directing light into the container from above. As an example, the method is carried out with an implement comprising a container having an opening at the top, a reflecting plate having a hole in its center and disposed above the container such that the light reflected by this reflecting plate enters the container, and a seat portion on which a gem is placed. The seat portion is located substantially in the center of the bottom of the container. The straight line connecting the seat portion with one fringe of the opening forms an angle of 20 to 50 degrees with the straight line connecting the seat portion with the opposite fringe of the opening.

37 Claims, 19 Drawing Sheets

METHOD AND IMPLEMENT FOR OBSERVING OR PHOTOGRAPHING GEM SUCH AS DIAMOND

FIELD OF THE INVENTION

The present invention relates to a method of observing or photographing the brilliancy of a gem, especially a diamond. The invention also relates to an implement used for such observation or photography.

BACKGROUND OF THE INVENTION

One of the reasons why diamonds are preferred as gems lies in their characteristic brilliancy. This brilliancy arises from the fact that light incident on a diamond is reflected internally by its cut facets, spectrally dispersed, and collected on the side of the crown, i.e., on the surface side. The diamond exhibits brilliancy in various colors because of the spectral dispersion inside it. Therefore, the degree of the brilliancy and the beautifulness of a diamond depend much on the quality of cutting and the proportions.

A diamond that is ideally brilliant cut for obtaining the highest brilliance is well proportioned, and the superfluous portions have been removed from it. The cut facets are oriented in correct directions. Most of the light incident on the diamond is regularly reflected internally by the cut facets and collected on the side of the crown. Consequently, the greatest and most splendid and varied brilliancy is shown.

On the other hand, a diamond that is roughly cut to derive the maximum carat is ill proportioned and has superfluous portions. The cut facets are oriented in random directions. Therefore, the incident light is not regularly reflected internally. Only a small portion of the light is collected on the side of the crown. For these reasons, the brilliancy is poor, and the jewel lacks splendor. In the case of an especially poorly cut diamond, the incident light may directly pass to the rear side, or the pavilion.

Normally, ordinary buyers observe diamonds with the naked eye in shops. The diamonds appear to exhibit almost identical brilliance irrespective of the quality of the cutting by the effects of the illumination. It is very difficult for those who have no expert knowledge to see whether the diamond has been cut satisfactorily.

Accordingly, the present situation is that manufacture and sale of diamonds rely mostly on their carats because carats can directly affect the prices. The quality of cutting and the proportions tends to be less adopted in evaluating gems since these factors cannot be easily judged as mentioned above.

A simple implement for observing the brilliance of diamonds has been proposed in Japanese Utility Model Laid-Open No. 109041/1985. In particular, a diamond of interest is placed between a magnifying glass and a light source. A red disk which is centrally provided with a hole is mounted to the side of the objective lens of the magnifying glass. The light from the light source is directed to the disk so that the light may be reflected to the diamond. If a large amount of red light is observed, then the gem is taken to be excellent in brilliance.

However, the fringes of the diamond observed with this implement are quite simple, i.e., composed of white, black, and one kind of red. Shining portions are red in color. Those portions which are not shining are white in color. It is impossible to know the nature of black portions. Usually, changes in the intensity of light should produce changes in the density of the fringes, but the fringes observed with this implement are uniform in density. Furthermore, no three-dimensional characteristics are observed. In this way, this known implement does not permit one to judge the brilliance of diamonds sufficiently precisely.

A photograph is attached to a written statement of an expert opinion on a diamond. This photograph is taken by a camera placed above the diamond while illuminating it from below. In the produced fringes, the brightest and least bright portions appear black to the naked eye, while the other portions appear whitish. This photograph has the following disadvantages.

(1) Those portions which should appear brightest are black like in a negative film of a black-and-white photograph.

(2) Those portions which should be brightest and those portions which are least bright are equally black in the resulting image. Therefore, it is completely impossible to know which portions are really bright.

(3) The white portions in the photograph should have contain portions of varied degrees of brightness. However, these varied degrees of brightness produce little changes in the density in this photograph. Hence, almost no difference in brightness can be seen in the white portions. This also totally deprives the fringes of three-dimensionality.

In this way, this photograph is very difficult for laymen to understand though this situation may not apply to experts.

As described previously, the brightness specific to diamonds depends not only on the amount of reflection of light inside the gems but also on emission of various colors due to spectral dispersion. Nonetheless, it is impossible for the unaided eye to see the extent of the variedness of the colors of the emitted light. Also, it has been impossible to pick up varied colors of light emitted from a diamond, using the above-described conventional implement or photography method.

Where a diamond is photographed in a conventional manner to prepare a catalog or the like, light is directed to the diamond from the side of the camera. In this photography, it is almost impossible to pick up the above-described varied colors from the diamond. In this manner, any photography or implement which makes it possible to catch various colors of light emitted by a diamond is not known.

SUMMARY OF THE INVENTION

It is an object of the present invention to provide a method of observation or photography which can catch the degree of brilliance and colors of light emitted by a gem, especially a diamond, to thereby permit even a layman to easily judge the proportions and the quality of the cutting.

It is another object of the invention to provide an implement used in the method described just above.

A method of observation or photography according to the invention comprises the steps of: placing a gem inside a container having an opening at the top in such a manner that light can enter the container only from directions lying in the range of angles of 20 to 50 degrees about the line vertical to the gem; directing light into the container from above; and observing or photographing the inside gem from above the container.

The step of directing light into the container can be carried out in two ways. In one way (1), a reflecting plate is placed above the container. Light coming from below is reflected into the container by the reflecting plate. In another way (2), an illuminating device is mounted above the container. The light emitted by this device is directly directed into the container.

In the former method (1), the reflecting plate has a hole in its center. This reflecting plate is placed above the container in such a way that light coming from below is reflected into the container. The gem inside the container can be observed or photographed from above through the hole in the reflecting plate. The method of directing light to the reflecting plate from below can be effected by either process i) or process ii) below.

i) Light coming from above is reflected either around the container or around the opening in the container and directed to the reflecting plate.

ii) The illuminating device is positioned either around the container or around the opening in the container. The light emanating from the device is made to impinge on the reflecting plate.

In the method i) above, natural light reflected around the container or around the opening in the container can be utilized. Alternatively, the illuminating device is placed above the container, and the light emitted by this illuminating device is reflected either around the container or around the opening in the container.

In the above-described method (1) using the reflecting plate, the reflecting surface of the reflecting plate is most preferably specular. However, it is possible that the reflecting surface of the reflecting plate is white or light in color or a glossy metal surface.

Where the reflecting surface of the reflecting plate is specular, it is most preferably composed of a plurality of small specular surfaces surrounding the aforementioned hole, the specular surfaces being so oriented that the light coming from the vicinities of the container or from the opening in the container is reflected into the container by the small specular surfaces.

Where the reflecting surface is a metal surface, it is preferably uneven.

In the method i) above, either the container or the opening in the container is preferably surrounded by a surface that is white or light in color or is a metal surface having a specular or glossy surface. The light reflected off this surface is directed to the overlying reflecting plate.

In this way, in the present invention, any of various methods can be adopted in guiding light into the container. In any case, it is important that a gem of interest be placed inside the container such that light enters it from only the directions lying within the range of angles of 20 to 50 degrees about the line vertical to the gem. In other words, the fringes of interest can be clearly seen only if the gem is placed in the container satisfying these conditions and if the gem is observed or photographed while positively directing the light into the container.

In one embodiment (i) of the implement for carrying out the above-described method according to the invention, the implement comprises a container having an opening at the top and a reflecting plate centrally provided with a hole. The reflecting plate is placed above the container in such a way that the reflected light enters the container. A seat portion on which a gem is placed is formed around the center of the bottom of the container. The straight lines connecting the seat portion with the opposite fringes, respectively, of the opening form an angle of 20 to 50 degrees with each other.

In another embodiment (ii) of the implement for carrying out the method, the implement comprises a container having an opening at the top, a reflecting plate centrally provided with a hole, and an illuminating device emitting light onto an upwardly facing surface around the container or onto an upwardly facing surface around the opening in the container. The reflecting plate is placed above the container in such a way that the reflected light enters the container. A seat portion on which a gem is placed is formed around the center of the bottom of the container. The straight lines connecting the seat portion with the opposite fringes, respectively, of the opening form an angle of 20 to 50 degrees with each other.

In a further embodiment (iii) of the implement for carrying out the method, the implement comprises a container having an opening at the top, a reflecting plate centrally provided with a hole, and an illuminating device disposed either around the container or around the opening in the container to emit light to the reflecting plate. The reflecting plate is placed above the container in such a way that the reflected light enters the container. A seat portion on which a gem is placed is formed around the center of the bottom of the container. The straight lines connecting the seat portion with the opposite fringes, respectively, of the opening form an angle of 20 to 50 degrees with each other.

In a yet other embodiment (iv) of the implement for carrying out the method, the implement comprises a container having an opening at the top and an illuminating device placed above the container in such a way that light enters the container. A seat portion on which a gem is placed is formed around the center of the bottom of the container. The straight lines connecting the seat portion with the opposite fringes, respectively, of the opening form an angle of 20 to 50 degrees with each other.

In the embodiments (i), (ii), and (iii) using the reflecting plate, the reflecting surface is most preferably specular. It is also possible that the reflecting surface is white or light in color. Moreover, the reflecting plate can have a reflecting glossy metal surface.

Where the reflecting surface of the reflecting plate is specular, the reflecting surface is most preferably composed of a plurality of small specular surfaces surrounding the hole. The small specular surfaces are oriented in such a way that light coming from the vicinities of the container or from the opening in the container is reflected into the container.

Where the reflecting surface is a metal surface, it is preferably uneven.

In the embodiments (i) and (ii) above, either the container or the opening in the container is preferably surrounded by a surface which is white or light in color or is a specular or glossy metal surface, so that the light reflected by this surface is directed to the overlying relfecting plate.

In the embodiment (iv) above, the illuminating device consists of a holder centrally provided with a hole and a plurality of illuminators mounted to the underside of the holder so as to surround the hole. Alternatively, the illuminating device consists of a holder centrally provided with a hole and an annular illuminator mounted to the underside of the holder so as to surround the hole.

Other objects and features of the invention will appear in the course of the description thereof which follows.

DETAILED DESCRIPTION OF THE INVENTION

Brilliance specific to diamond is attributable to both reflection at the surface and internal reflection. Surface reflection occurs also with glass or other similar materials. In the case of diamond, a large portion of the light incident from the surface is refracted and reflected at the cut facets such as bottom surfaces. In addition, the light is spectrally dispersed inside the gem. Thus, brilliancy specific to diamond takes place. As described previously, the amount of the light reflected internally and the spectral dispersion are determined by the quality of the cutting and the proportions. Cutting and proportions are most important to obtain splendor and great brilliance.

In the method according to the invention, light is directed into a container from above. The light enters the container only from directions lying within the range of angles of 20 to 50 degrees about the vertical to the diamond under examination and then hits the diamond. The light is partially reflected at the surfaces on the side of the crown. Some of the light is internally reflected back to the side of the crown. Depending on the quality of the cutting of the diamond, a portion of the light passes to a seat portion on which the gem is placed. The light reflected at the surfaces on the side of the crown and the light returned to the side of the crown due to internal reflection arrive at the observer's eye or camera lens.

The image of the diamond observed or photographed by the novel method in this way exhibits characteristic fringe patterns and colors according to the quality of the cutting and the proportions. Therefore, it is possible to check the degree of the brilliance of the diamond, the quality of the cutting and the proportions at a glance. The operation and the advantages of the invention will appear also from the actual examples of photographs associated with the examples of the invention described later.

The principle on which the observed image of the diamond exhibits clear fringe patterns and colors as described above is not fully understood but can be explained away as follows. Light is caused to positively impinge on the diamond by the use of a reflecting plate or the like. The region of the gem hit by the light is restricted by the container. As a result, light is made to hit the diamond from appropriate directions.

Figure 1:
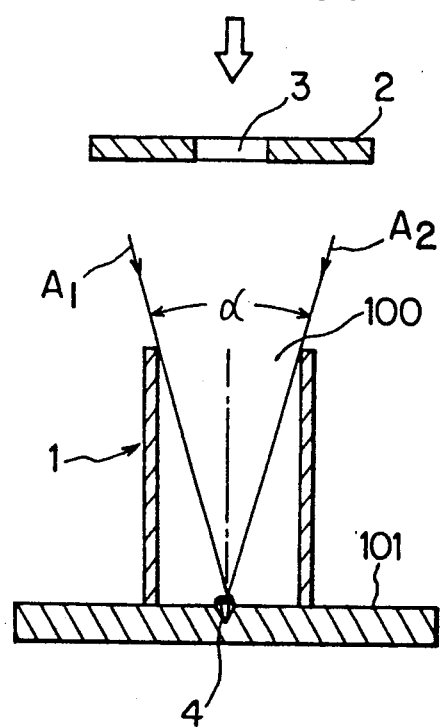
FIG. 1 is a view illustrating an experiment performed to ascertain the effects of the method according to the invention.

The present inventor made an observation to check the effects and advantages of the invention. Referring to FIG. 1, several kinds of cylindrical container 1 (only one is shown) which differed in ratio of the inside diameter D to the height H were used. The upper surface 101 around each container 1 was white. A white plate 2 having a hole 3 extending through it was placed above the container. A diamond 4 was placed in the center of the inside bottom of the container 1. The observation was made through the hole 3. It has been found that where the angle $\alpha$ formed between the straight line $A_1$ connecting the center of the inside bottom of the container 1 with one fringe of the opening 100 in the container 1 and the straight line $A_2$ connecting the center of the inside bottom of the container with the opposite fringe of the opening 100 was outside the range of angles of 20 to 50 degrees, the above-described fringes could not be easily seen. Specifically, where the angle $\alpha$ was less than 20 degrees, then the diamond appeared blackish as a whole. Even for the diamonds cut well, neither the fringe patterns nor the colors could be clearly observed. Where the angle $\alpha$ was in excess of 50 degrees, the diamond was excessively brilliant as a whole. Also in this case, neither the fringe patterns nor the colors could be clearly observed. If the angle $\alpha$ is too large, i.e., the inside diameter of the container 1 is too large compared with the height, then the region of the diamond hit by the light is too broad. Conversely, if the angle $\alpha$ is too small, i.e., the inside diameter of the container 1 is too small compared with the height, then the region of the diamond hit by the light is too narrow. This reduces the amount of the incident light. We estimate that the formation of the aforementioned fringes and the colors needs incidence of a critical amount of light and that in either case this incidence is not realized. Experiments have revealed that where the angle $\alpha$ is 20 to 50 degrees, especially approximately 30 degrees, the vividest fringes and colors appeared irrespective of the size of the container 1.

Accordingly, in the present invention, the angle $\alpha$ made between the straight lines $A_1$ and $A_2$ connecting the center of the inside bottom of the container 1 with the opposite fringes, respectively, of the opening 100 in the container 1 is set to 20 to 50 degrees, preferably 30 to 40 degrees.

In the present invention, it is necessary to positively direct light into the container from above. For this purpose, a reflecting plate or illuminating device is normally disposed above the container. We have confirmed the following points by performing experiments.

i) Introducing natural light, i.e., sunlight or indoor light consisting mainly of sunlight, into the container by the use of a reflecting plate rather than an illuminating device permits one to observe more splendid fringes and colors.

ii) Where a reflecting plate is employed, the reflecting plate can consist of a plurality of small specular surfaces surrounding the hole. Therefore, light can be effectively directed into the container from numerous light sources. Vivider and more splendid fringes can be obtained than in the case where the reflecting plate has only one reflecting surface.

iii) Where light is directed into the container, the brilliance is moderately suppressed and vivid and splendid fringes can be obtained by once reflecting the light off a white, whitish (e.g., milk white), or light-colored surface before the light enters the container rather than by directing natural light or the light emitted from an illuminating device into the container directly or via a mirror. The reason of this is not clear, but we estimate that the reflection at the whitish surface gives rise to the wavelengths of light suitable for the development of the fringes.

iv) Where the light emitted from an illuminating device is directed into the container, the brilliance of the fringes is suppressed more by using a fluorescent lamp as the illuminating device than in the case in which incandescent lamps are used.

v) Where it is desired to impart brilliance to a part of the fringes to symbolize the brilliance of the diamond in view of the facts iii) and iv) above, for enhancing the visual effect, light reflected by a white, whitish, or light-colored surface or the light emitted from a fluorescent lamp is preferably directed into the container. At the same time, the light from incandescent lamps is directed into the container directly or via a reflecting mirror.

In the novel observation method, magnified fringes of the diamond can be observed by disposing a magnifying lens in or over the hole formed in the reflecting plate. In this way, the fringes are very easy to see. Also, it is easy to judge the fringes.

In the novel method of observation or photography described thus far, fringes that are created from a diamond and consist of various colors well corresponding to the degree of the brilliance and also to the colors of light due to spectral dispersion specific to the diamond can be observed or photographed, which would have been heretofore impossible to realize. Hence, even a layman can easily judge the degree of brilliance and splendor attributed to the quality of the cutting of the diamond and the proportions.

In a photograph of a diamond taken by the prior art photography method, those portions which are most brilliant in practice appear black. Therefore, this method has the fatal disadvantage that an ordinary person cannot visually know the correspondence to the brilliance of a diamond. In the novel photography method, however, a picture of a diamond can be taken which well represents the actual brilliance. This photograph is quite useful as a written statement of an expert opinion on a diamond. Additionally, the novel implement can carry out the novel method easily. Various examples of the invention are hereinafter described.

Figure 2:
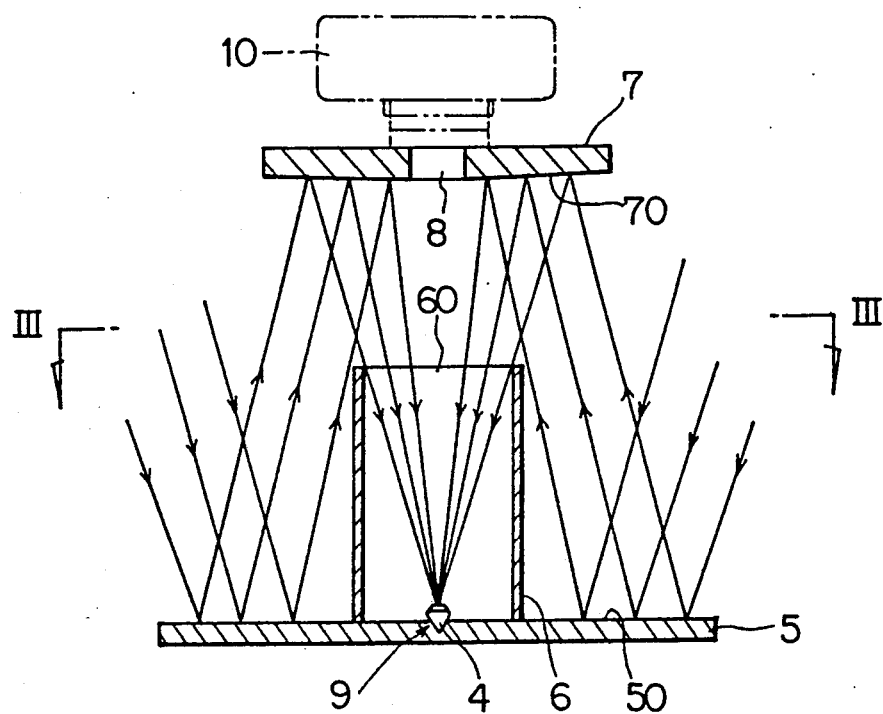
FIG. 2 is a vertical cross section of an implement according to the invention.
Figure 3:
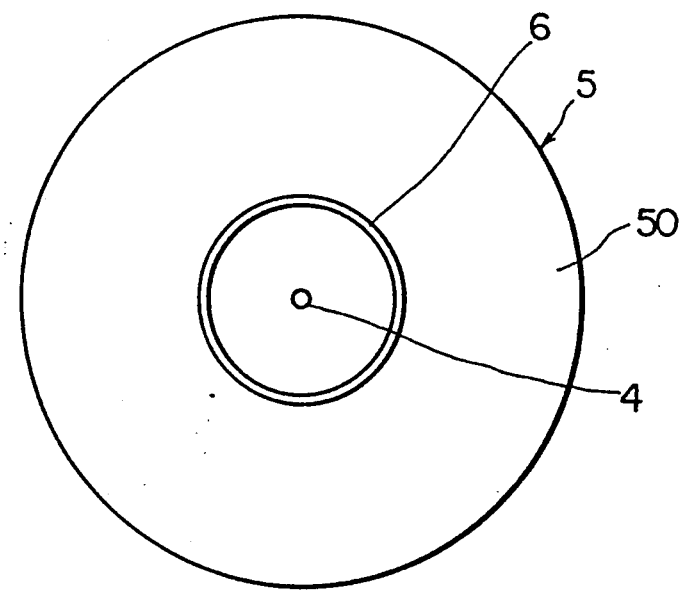
FIG. 3 is a plan view taken along the line III—III of FIG. 2.

Referring to FIGS. 2 and 3, there is shown an implement according to the invention. This implement is designed to carry out the novel method, and comprises a base 5, a cylindrical container 6 installed in the center of the base 5, and a reflecting plate 7 disposed above the container. The upper surface of the base 5 is white in color so that light coming from above may be reflected toward the reflecting plate 7 located above the container 6.

The container 6 has an opening 60 at the top. A seat portion 9 on which a gem is placed is formed in the center of the inside bottom of the container. Where the gem under observation is a naked stone, the seat portion 9 is preferably concave to permit the gem to be placed stably. Where the gem is attached to an adornment such as a finger ring, the structure of the seat portion preferably is capable of holding the adornment.

The container 6 is so built that the angle $\alpha$ made between the two straight lines (FIG. 1) connecting the seat portion 9 with the opposite fringes, respectively, of the opening 60 is set to 20 to 50 degrees, preferably 30 to 40 degrees. The height and the diameter of the opening 60 are selected to fulfil this condition.

The lower surface 70 of the reflecting plate 7 is specular. The light reflected by the upper surface of the container 6 is reflected into the container 6 by the lower surface 70. Therefore, the specular lower surface 70 is tilted radially. This reflecting plate 7 is supported to the base 5 by appropriate support means (not shown). The reflecting plate 7 is centrally provided with a hole 8 extending through it. The diamond on the seat portion 9 inside the container 6 can be observed or photographed through this hole 8.

In order to photograph the diamond using this implement, the diamond 4 is placed on the seat portion 9. A camera 10 is placed on the hole 8 in the reflecting plate 7, and then a photograph is taken. A visual observation is made through the hole 8.

Referring to FIG. 2, the lower surface 70 of the reflecting plate 7 is most preferably specular. The lower surface can also be white, whitish, or light-colored surface, glossy metal surface, or any other surface which well reflects light or is made from a material that reflects light well.

Where the lower surface 70 is a metal surface, it is preferably uneven to introduce a sufficient amount of light into the container 6. In this case, it follows that a number of small reflecting surfaces directing light into the container 6 are formed due to the unevenness. This assures that a sufficient amount of light enters the container.

Most preferably, the upper surface 50 of the base 5 is white or light whitish in color. It is also possible that the upper surface is a specular surface, metal surface, or other surface showing a high reflectivity.

In summary the lower surface 70 of the reflecting plate 7 and the upper surface 50 of the base 5 have preferably high reflectivities to introduce the maximum possible proportion of the light coming from above into the container 6. As described already, however, the light is preferably reflected by a white or whitish light-colored surface before the light passes into the container 6. For this purpose, any one of the upper surface 50 of the base and the lower surface 70 of the reflecting plate is preferably a white or whitish light-colored surface, while the other is a specular surface that shows the highest reflectivity. The most preferred structure is the example shown in FIGS. 2 and 3.

Figure 4:
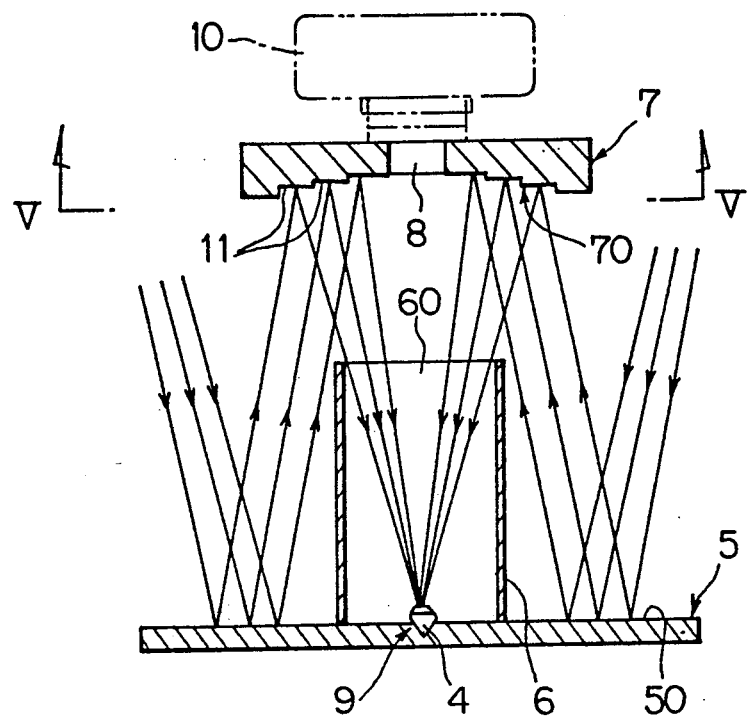
FIG. 4 is a vertical cross section of another implement according to the invention.
Figure 5:
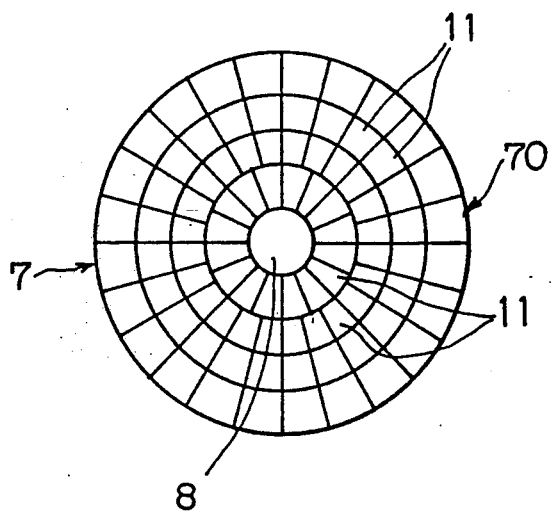
FIG. 5 is a plan view taken along the line V—V of FIG. 4.

FIGS. 4 and 5 show a more preferred example of the invention. The lower surface 70 of the reflecting plate 7 is composed of a plurality of small specular surfaces 11 surrounding the hole 8 extending through the plate. The specular surfaces 11 are so oriented that light coming from below, or from the upper surface 50, is reflected into the container 6. In this case, the numerous small specular surfaces 11 form light sources. Light can be effectively directed into the container from the numerous light sources. The derived fringes are vivider and more splendid than the case in which the reflecting surface of the reflecting plate consists of one surface. This example is similar in structure to the example described already in connection with FIG. 2 in other respects. The upper surface 50 of the base 5 can adopt any one of the various structures described in connection with FIG. 2.

In the examples described thus far, natural light is directed into the container 6. Examples shown in FIGS. 6, 7, 8, and 9 are principally intended to direct the light emitted by an illuminating device into the container 6.

Figure 6:
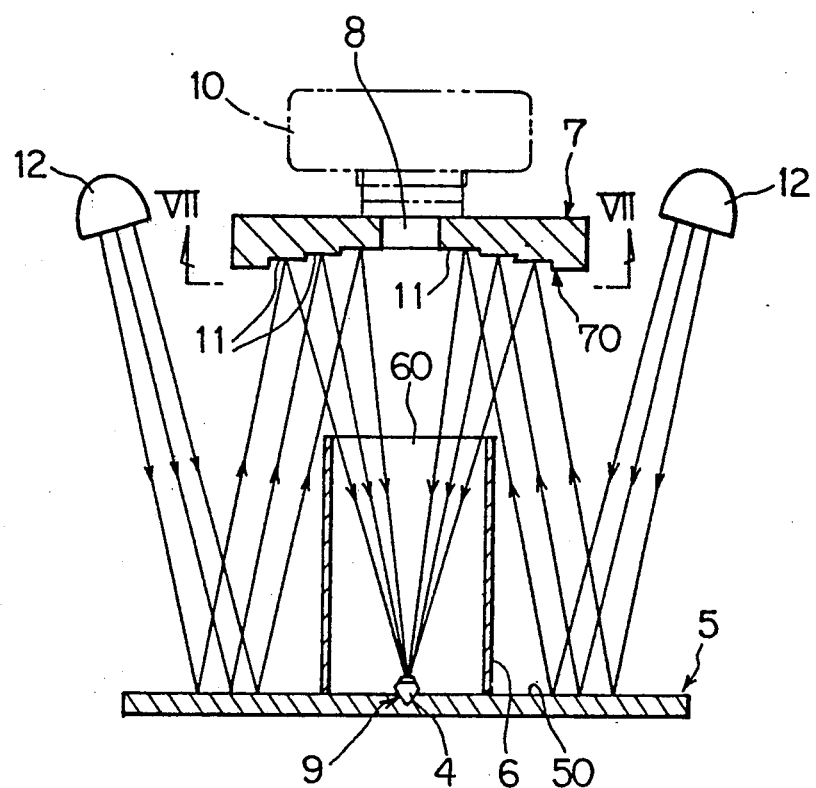
FIG. 6 is a vertical cross section of a further implement according to the invention.
Figure 7:
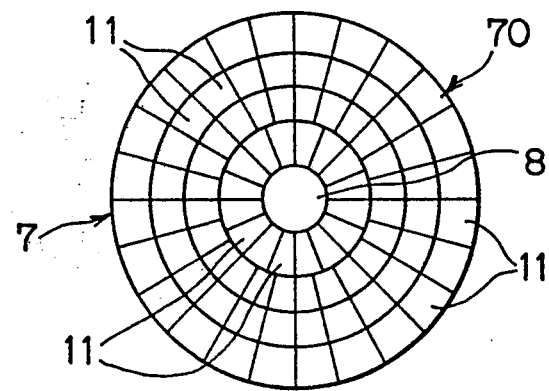
FIG. 7 is a plan view taken along the line VII—VII of FIG. 6.

In the example shown in FIGS. 6 and 7, an illuminating device 12 is disposed above the container 6. The light from the illuminating device is caused to impinge on the upper surface 50 of the base 5. The light reflected by the upper surface 50 is made to hit the lower surface 70 of the reflecting plate 7. In this example, the illuminating device located above the base 5 consists of a plurality of incandescent lamps. Instead, an annular fluorescent lamp can be disposed. This example is similar in structure to the example shown in FIG. 5 in other respects. Although the lower surface 70 of the reflecting plate 7 consists of small specular surfaces 11, this lower surface 70 and the upper surface 50 of the base 5 can have any of the various structures described already in connection with FIG. 2.

Figure 8:
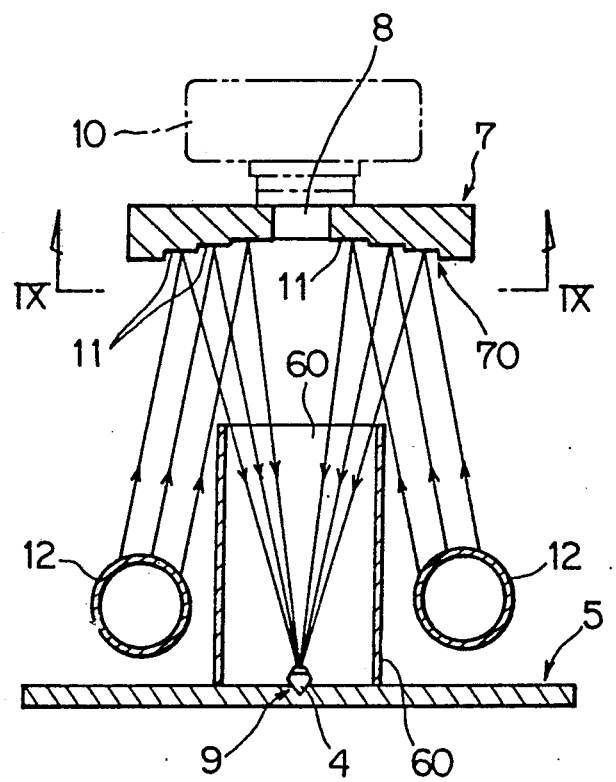
FIG. 8 is a vertical cross section of a yet other implement according to the invention.
Figure 9:
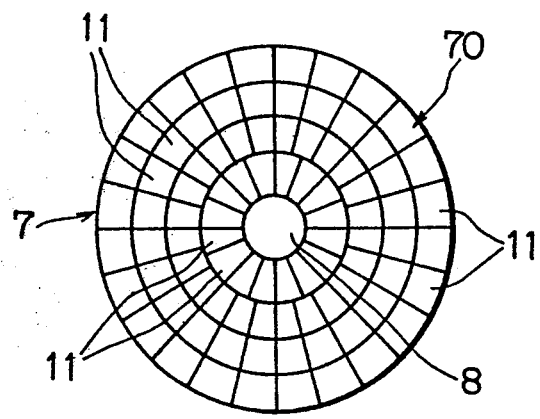
FIG. 9 is a plan view taken along the line IX—IX of FIG. 8.

In the example shown in FIGS. 8 and 9, an illuminating device 12 is disposed over the base 5 around a container 6. The light from the illuminating device 12 is made to fall on the lower surface 70 of the reflecting plate 7. In this example, the illuminating device 12 is an annular fluorescent lamp. Instead, the device can be made up of plural incandescent lamps. In this example, no limitations are imposed on the color or the material of the upper surface 50 of the base 5. This example is similar in structure to the example shown in FIG. 5 except for the upper surface 50 of the base 5. Although the lower surface 70 of the reflecting plate 7 consists of small specular surfaces 11, the lower surface 70 can have any of the various structures described already in connection with FIG. 2.

In all of the above examples, light is directed into the container 6 by the use of the reflecting plate 7. In examples shown in FIGS. 10 and 11, the light from the illuminating device is directly directed into the container 6.

Figure 10:
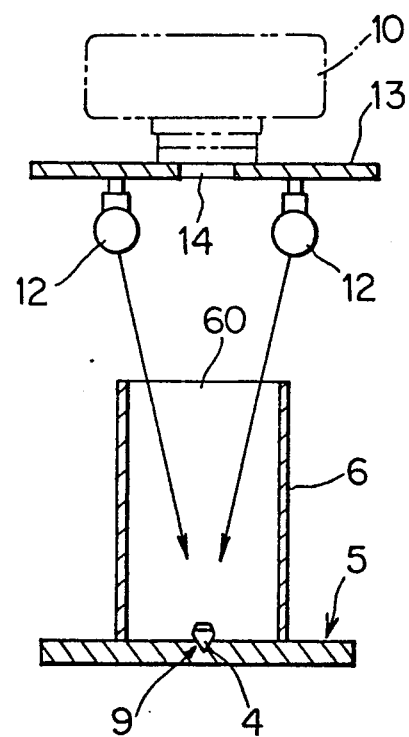
FIG. 10 is a vertical cross section of a yet further implement according to the invention.

In the example shown in FIG. 10, a holding plate 13 having a hole 14 in its center is disposed above the container 6. An illuminating device 12 consisting of incandescent lamps are mounted to the underside of the holding plate 13, which is supported to the base 5 by appropriate support means (not shown).

Figure 11:
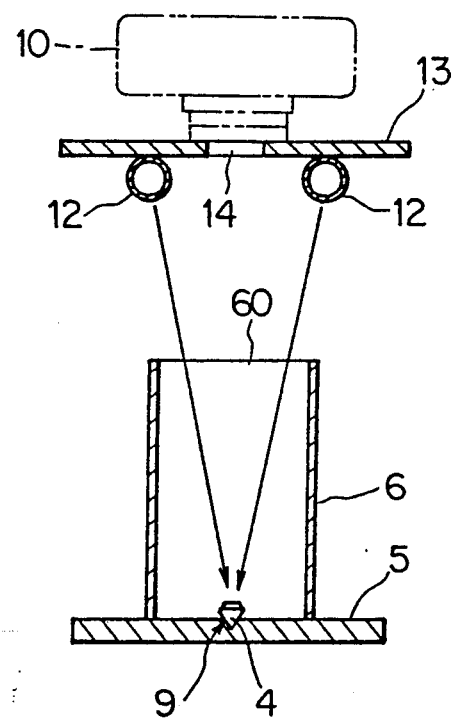
FIG. 11 is a vertical cross section of a still further implement according to the invention.

In the example shown in FIG. 11, a holding plate 13 similar to the aforementioned holding plate 13 is mounted. An illuminating device 12 consisting of an annular fluorescent lamp is mounted to the underside of this holding plate 13.

In both of the examples shown in FIGS. 10 and 11, the light emitted by the illuminating device 12 directly enters the container 6. In these two examples, the container 6 is similar in structure to the container used in the previous examples.

In any of the above examples, the container 6 is cylindrical. It is to be noted that no restrictions are placed on the shape of the container 6 as long as the angle $\alpha$ lies within the range of angles of 20 to 50 degrees.

Figure 12:
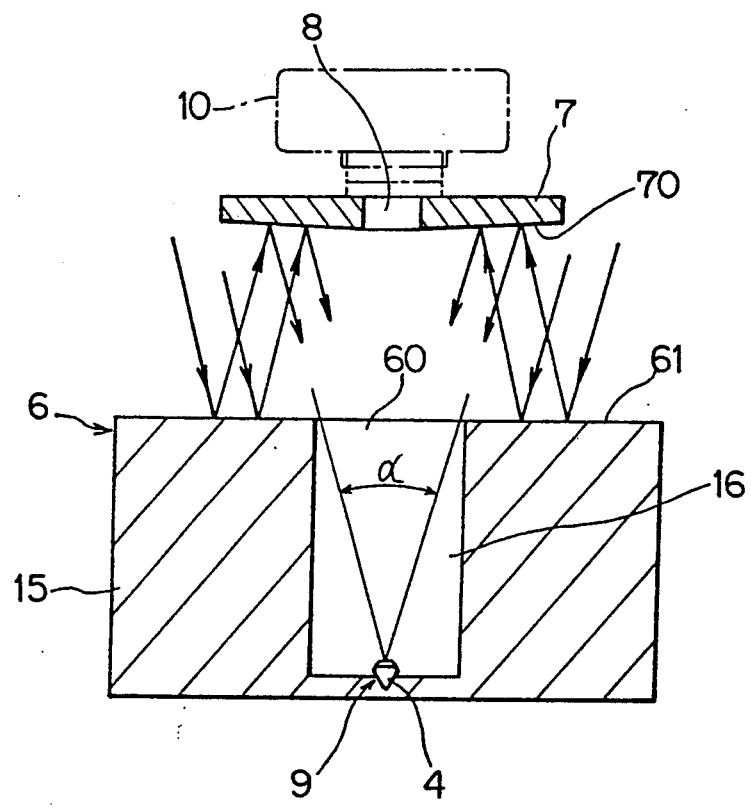
FIG. 12 is a vertical cross section of an additional implement according to the invention.
Figure 13:
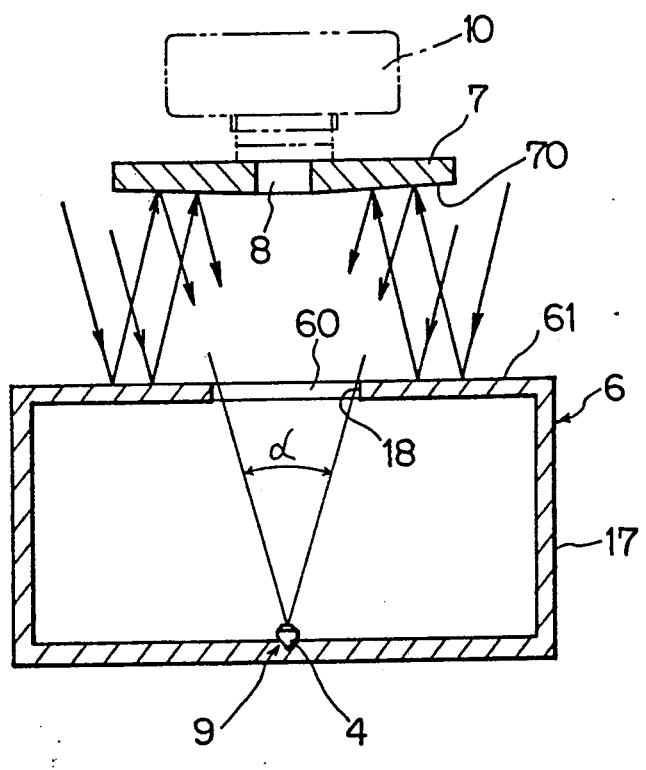
FIG. 13 is a vertical cross section of a still other implement according to the invention.

Referring to FIG. 12, the container 6 is a member 15 which is centrally provided with a recess 16. Referring to FIG. 13, the container 6 is a boxlike member 17 that is centrally provided with a circular hole 18. In this way, the container 6 can be configured at will.

Figure 14:
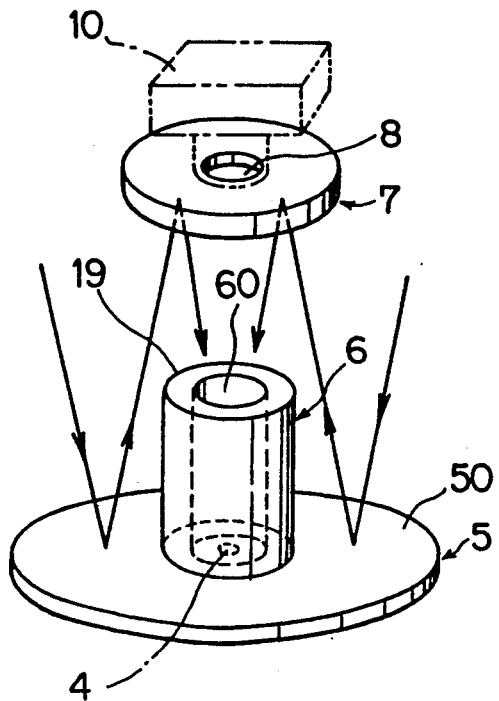
FIG. 14 is a vertical cross section of a yet additional implement according to the invention.
Figure 15:
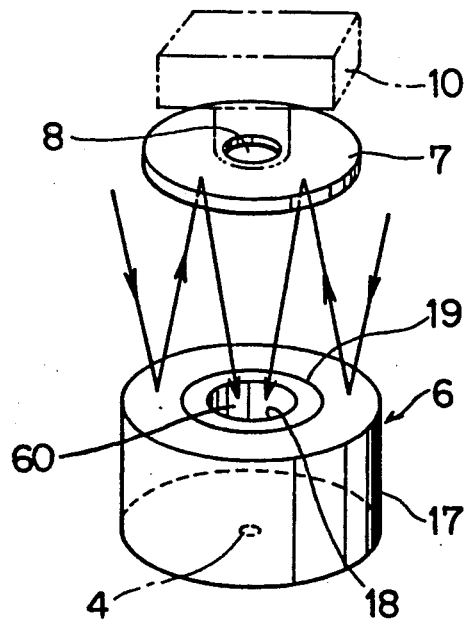
FIG. 15 is a vertical cross section of an even additional implement according to the invention.

In the examples shown in FIGS. 12 and 13, the container 6 acts also as the base. Where light is introduced into the container in the same way as in the examples shown in FIGS. 2, 4, and 5, light is reflected to the reflecting plate 7 by the upper surface 61 around the opening 60. Therefore, the upper surface 61 can be made similar in structure including the color and the material to the upper surface 50 of the base 5 already described in conjunction with FIG. 2.

Where a photograph is taken by a camera, extraneous light should not enter the camera lens from around the opening 60. For this purpose, as in the examples shown in FIGS. 14 and 15, a certain region 19 surrounding the opening 60 is preferably a black or blackish portion which shows a low reflectivity. For example, black cloth is stuck on this portion.

In the above examples, the upper surface of the reflecting plate 7, at least the surroundings of the hole on which the camera lens bears, is preferably a black or blackish portion having a low reflectivity.

Figure 16:
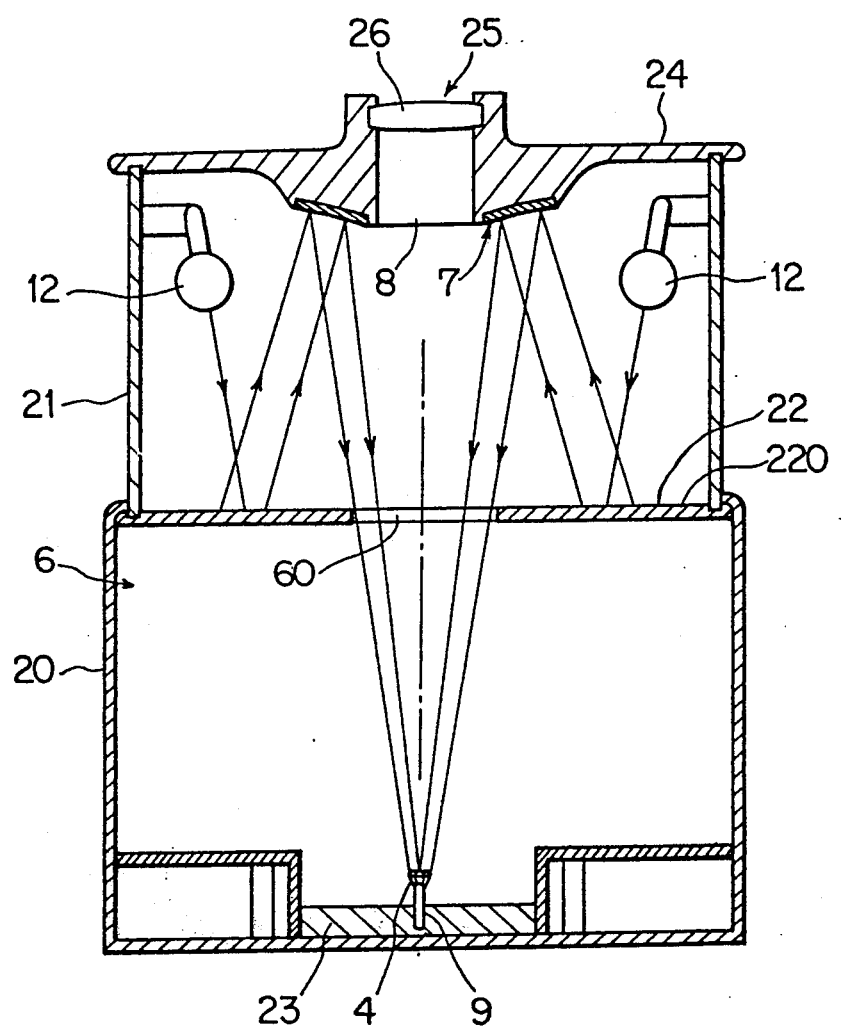
FIG. 16 is a vertical cross section of an even other implement according to the invention.
Figure 17:
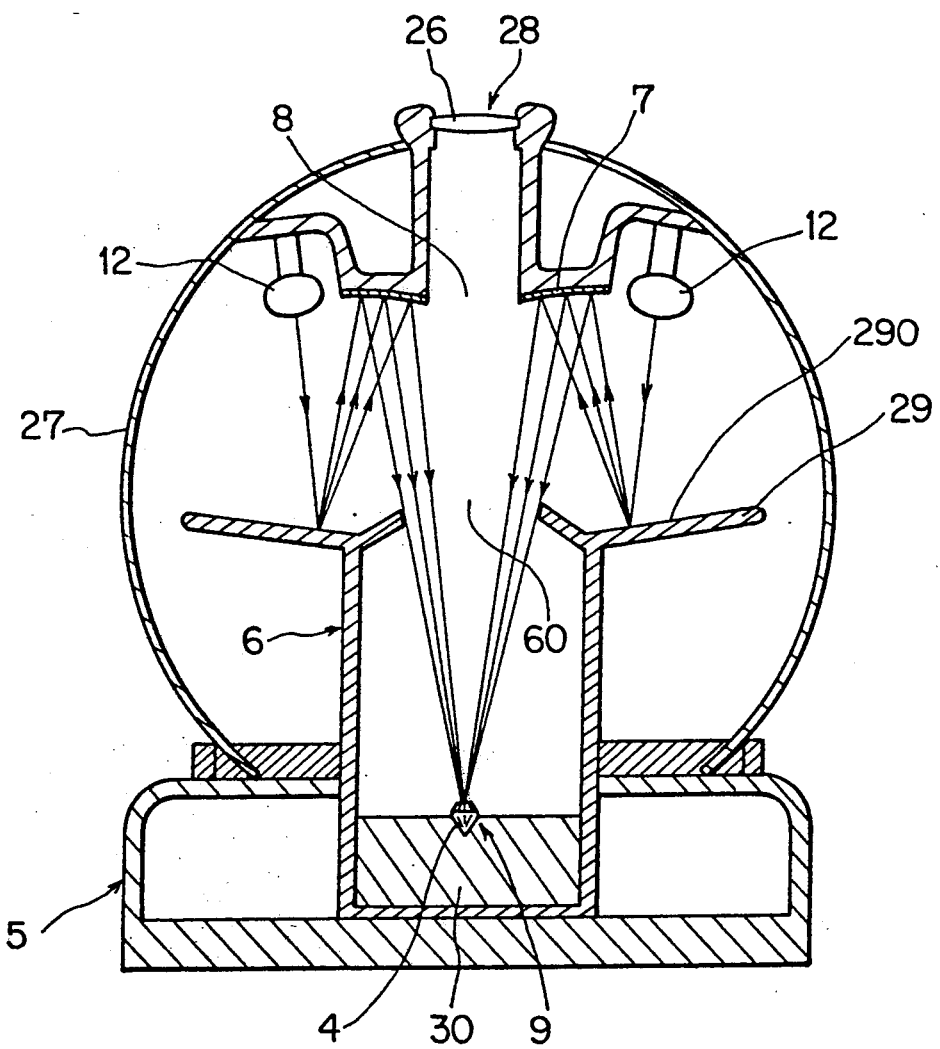
FIG. 17 is a vertical cross section of an even further implement according to the invention.
Figure 18:
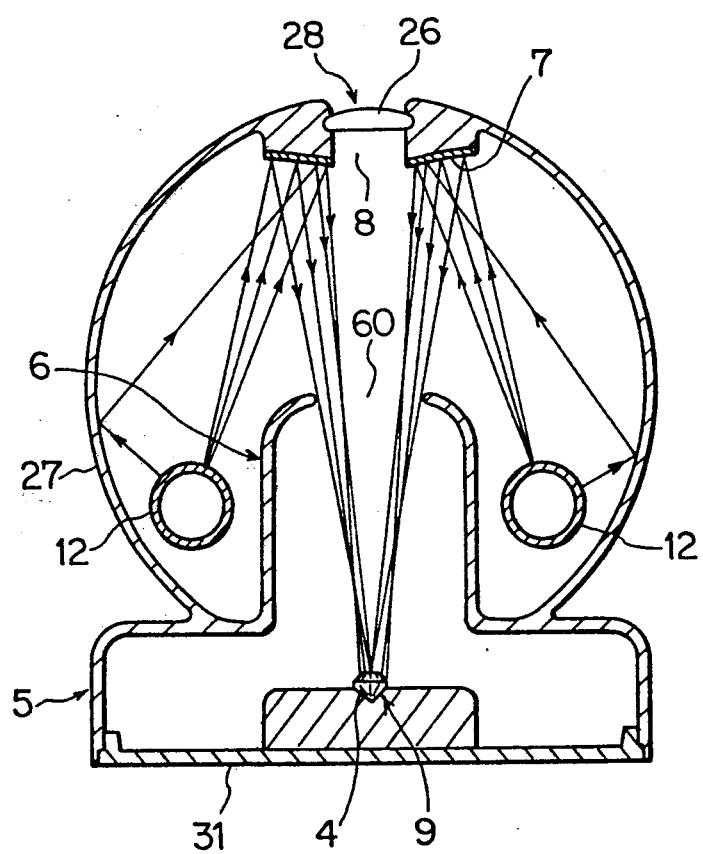
FIG. 18 is a vertical cross section of even another implement according to the invention.

FIGS. 16-18 show implements used only to observe a diamond, for example, for displaying it. These implements are intended to be employed in a jewelry shop into which only a small amount of natural light enters.

The implement shown in FIG. 16 is extensible and comprises an outer cylindrical member 20 and an inner cylindrical member 21 fitted in the outer cylindrical member so as to be vertically slidable from the top of the outer cylindrical member.

The inner cylindrical member 21 has an inner flange 22 at its lower end. When the inner cylindrical member 21 is slid upward with respect to the outer cylindrical member 20, the outer cylindrical member 20 and the inner flange 22 together form a container 6. A hole formed in the inner flange 22 forms an opening 60. The upper surface 220 of the inner flange 22 is white in color.

A seat portion 9 on which a gem is placed is formed in the center of the inside bottom of the outer cylindrical member 20. In the present example, a pullout portion 23 which can be taken out is mounted at the bottom of the outer cylindrical member 20. The seat portion 9 is mounted on this pullout portion 23. In this example, what is observed is a diamond 4 attached to a finger ring. The seat portion 9 is provided with a groove in which the body of the finger ring can be fitly inserted.

A cover plate 24 having an observation port 25 in its center is mounted at the upper end of the inner cylindrical member 21. A magnifying lens 26 is mounted in the observation port 25. A reflecting plate 7 having a hole 8 in its center is mounted to the underside of the cover plate 24 around the observation port. In this example, the reflecting plate 7 is a mirror. An illuminating device 12 is mounted above in the inner cylindrical member 21.

In the example shown in FIG. 17, a spherical casing 27 is mounted on the base 5. A cylindrical container 6 integral with the base 5 is mounted inside the casing 27. An observation port 28 having a magnifying lens 26 is formed at the upper end of the casing 27. A reflecting plate or mirror 7 having a hole 8 in its center is mounted below the observation port. An illuminating device 12 is disposed around the reflecting plate 7. A flange 29 is formed around the upper end of the cylindrical container 6 to receive the light from the illuminating device 12 and to reflect it to the overlying reflecting plate 7. The upper surface 290 of the flange 29 is white in color. Also in this example, the base 5 has a pullout portion 30 that can be taken out. The seat portion 9 is mounted on this pullout portion 30.

The example shown in FIG. 18 has a casing 27 similar to the casing of the example shown in FIG. 17. A container 6 integral with the base 5 is mounted inside the casing 27. An illuminating device 12 consisting of an annular fluorescent lamp is mounted around this container 6. In this example, the inner surface of the casing 27 is white. The light from the illuminating device 12 directly strikes the reflecting plate 7. In addition, the light is reflected by the inner surface of the casing 27 and then impinges on the reflecting plate 7. The base 5 has a bottom plate 31 that can be detached. A seat portion 9 is mounted on the upper surface of the bottom plate 31.

Figure 19:
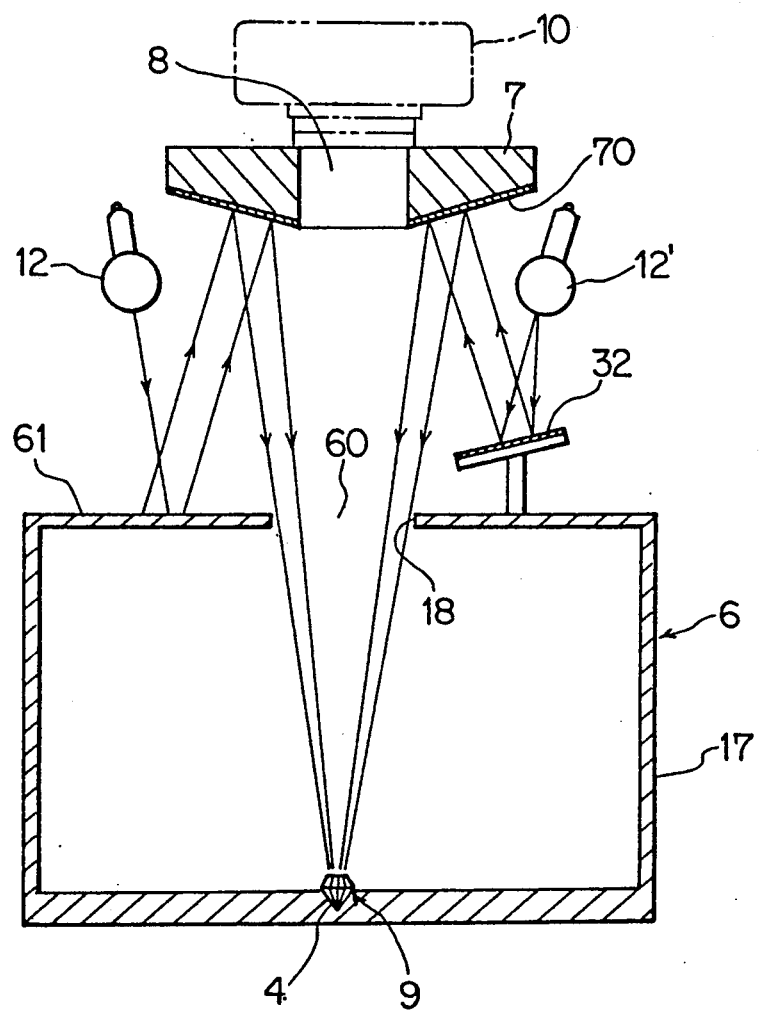
FIG. 19 is a vertical cross section of a yet even other implement according to the invention.
Figure 20:
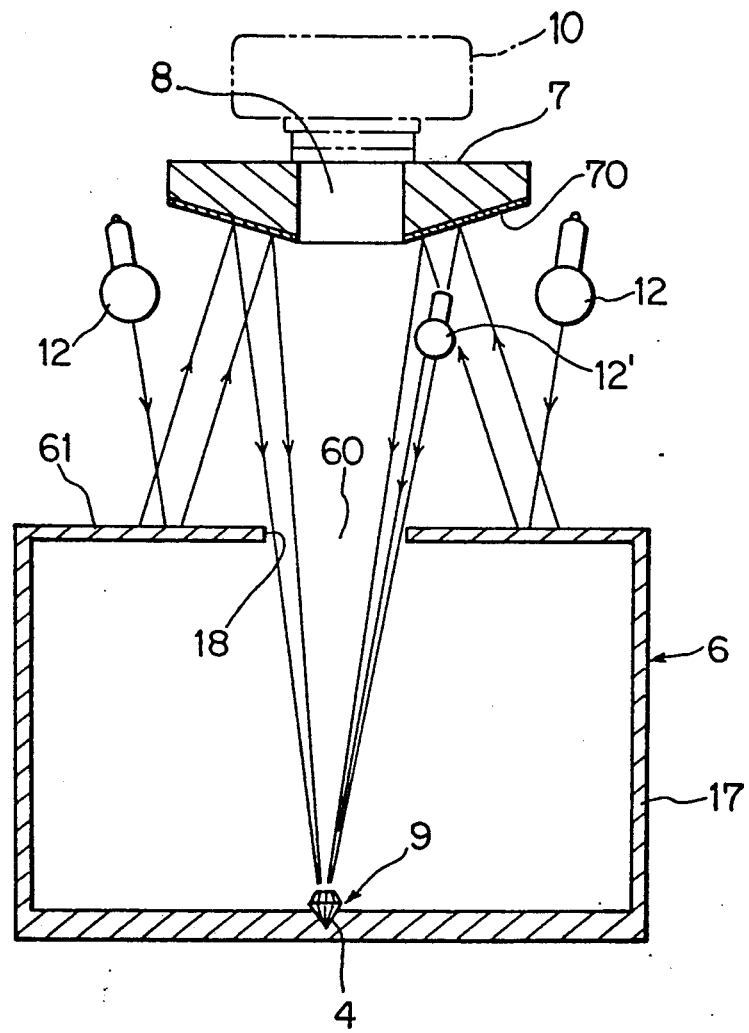
FIG. 20 is a vertical cross section of a yet even further implement according to the invention.
Figure 21:
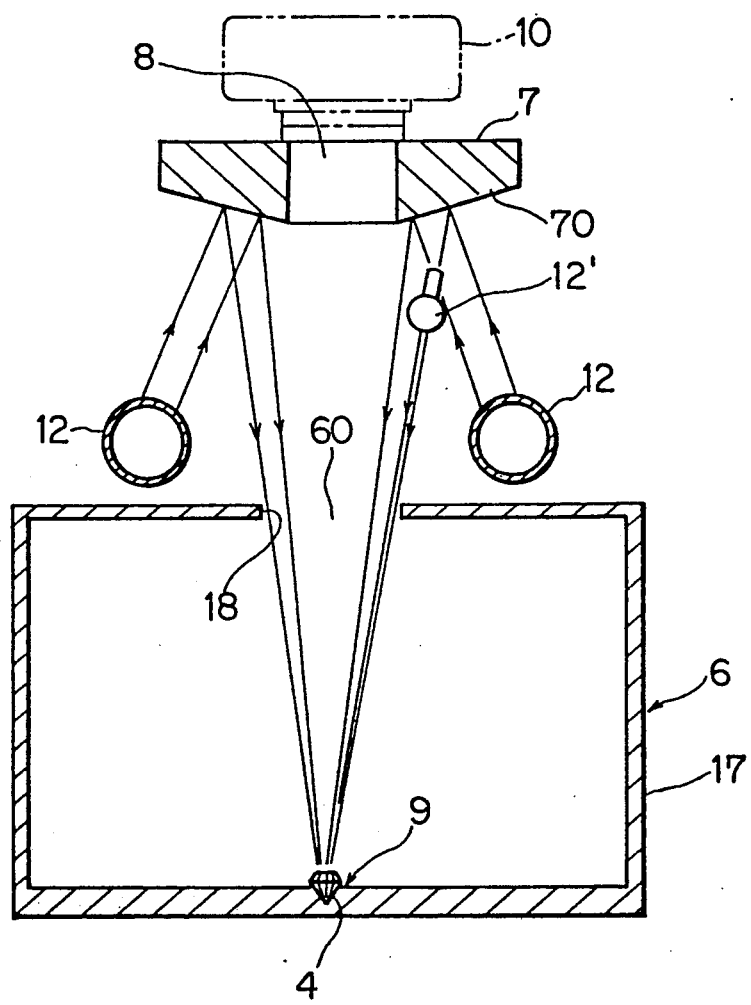
FIG. 21 is a vertical cross section of a yet even additional implement according to the invention.

As described above, in the present invention, when light is directed into the container, vivider and more splendid fringes can be obtained with the brilliance appropriately suppressed, by once reflecting natural light or the light emitted from an illuminating device by a white or light-colored surface before the light enters the container rather than by directly introducing the light into the container. Where it is desired to impart brilliance to a part of the fringes to symbolize the brilliance of the diamond for producing a visual effect, the light is reflected by a white or light-colored surface before the light enters the container. Additionally, the light from the illuminating device or incandescent lamps is directed into the container directly or via a reflecting mirror. FIGS. 19-21 show examples for obtaining such fringes.

Referring to FIG. 19, the lower surface of a reflecting plate 7 is specular. The light from an illuminating device 12 is reflected by the upper surface 61 of a container 6 to the overlying reflecting plate 7, whence the light is made to enter the container 6. The color of the upper surface 61 is white, whitish, or other light color. A small mirror 32 is mounted over the upper surface 61 of the container. The light from an illuminating device 12' or incandescent lamps is reflected by this small mirror 32 to the overlying reflecting plate or mirror 7, whence the light is guided into the container 6.

When it is desired to brighten only a part of the observed fringes, the amount of incidence of the light arising from the illuminating device 12' should be made sufficiently small compared with the amount of incidence of the light emanating from the illuminating devices 12. For instance, where the illuminating devices 12 are incandescent lamps, these illuminating devices 12, e.g., 3 incandescent lamps, are disposed around the opening 60. One small mirror 32 and one illuminating device 12' are provided. In this case, only one "arrow" of the fringes can be brightened as described later. Accordingly, when some arrows can be brightened, the number of illuminating devices 12' can be adequately selected according to the number of the brightened arrows. Where the illuminating device 12 is an annular fluorescent lamp, the small mirror 32 and the illuminating device 12' consisting of incandescent lamps are disposed under the same conditions as the foregoing.

In the example of FIG. 19, the light from the illuminating device 12' is reflected into the container 6 by the small mirror 32 and the reflecting plate 7. In the example of FIG. 20, the light from the illuminating device 12' is directly directed into the container 6. In this case, the number of the illuminating devices 12' and other conditions are the same as the conditions used for the above examples.

Referring to FIG. 21, the reflecting lower surface of the reflecting plate 7 is not specular, but the color of this surface is white, whitish, or other light color light color. The light from the illuminating devices 12 is reflected into the container 6 by this reflecting surface. In this case, the light from the illuminating device 12' is directly directed into the container 6.

Figure 22:
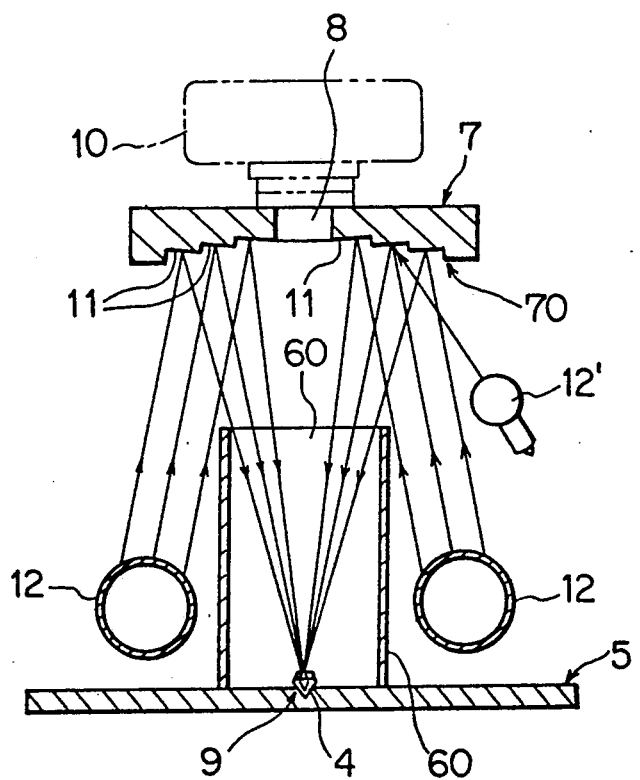
FIG. 22 is a vertical cross section of a yet still additional implement according to the invention.

As described previously, when the light from the illuminating devices is directed into the container directly or via a mirror, the brilliance of the fringes is suppressed to a larger extent by a fluorescent lamp than the case in which incandescent lamps are employed. In this way, where the light from the illuminating devices is directed into the container directly or via a mirror, it is desired to impart brilliance to a part of the fringes to symbolize the brilliance of the diamond for producing a visual effect, then the light from the fluorescent lamp is made to enter the container. Also, the light from the incandescent lamps is caused to enter the container. FIG. 22 shows one example for obtaining such fringes.

In the example of FIG.22, an illuminating device 12 consisting of an annular fluorescent lamp is disposed around the container 6. The light from the lamp is reflected into the container 6 by the specular lower surface of the overlying reflecting plate 7. Also, the light from illuminating devices 12' consisting of incandescent lamps is reflected into the container 6 by the reflecting plate 7. As described already in connection with FIG. 19, the number of the illuminating devices 12' and other factors are appropriately selected according to the desired degree of brilliance.

Obviously, the novel photography method is carried out by a dedicated photographic apparatus consisting of the novel implement in which a camera itself is incorporated. That is, the reflecting plate and so on are integral with the camera lens.

EXAMPLES OF PHOTOGRAPHY

Figure 23A:
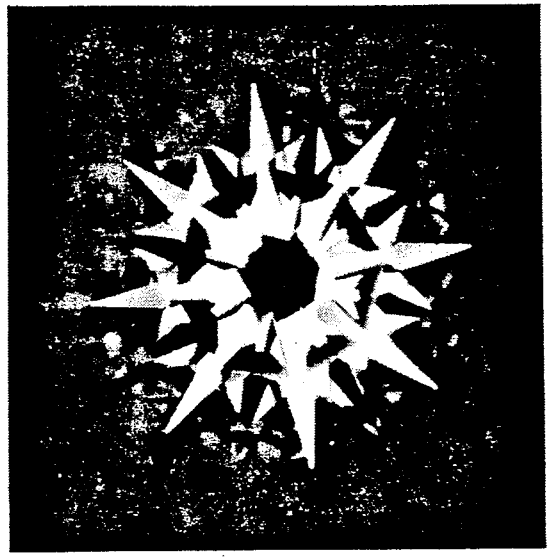
FIGS. 23(A) and 23(B) are photographs of diamonds taken by a method according to the invention.
Figure 23B:
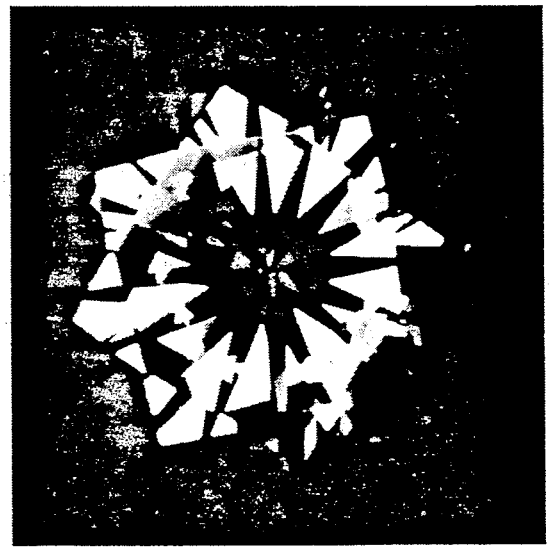

FIGS. 23(A) and 23(B) are photographs of two diamonds taken by the novel method. These photographs were taken on the sides of the crowns. These diamonds were almost identical in carat and diameter. Although they are black-and-white photographs, color photographs are taken in practice (see the reference photographs).

For the photography, a reflecting plate having a white lower surface was used. Light emitted by a fluorescent lamp was directed to this reflecting plate. Where the lower surface of the reflecting plate is specular, black-and-white photographs cannot sufficiently clearly represent fringes created from diamonds. For the fringes caught by this novel photography method, please see the color photographs which have been submitted as reference photographs.

It is possible to observe quite characteristic fringes consisting of various colors on the photographs of FIGS. 23(A) and 23(B), the colors being created by reflected light spectrally dispersed inside the diamonds.

Of these photographs, the diamond shown in FIG. 23(A) is almost ideally brilliant cut. The amount of reflection of light inside the gem is large. If it is observed by the eye in a conventional manner, a quite large amount of brilliance can be seen. Various colors are emitted from this diamond. The colors of the fringes of the diamond shown in FIG. 23(A) include white, black, and various colors due to spectral dispersion. Of these portions of the diamond, the white portions are considered to reflect light to the greatest extent. This brilliant cut diamond which has such ideal proportions has a very clear arrow-shaped white pattern extending radially from the center in 8 directions. Also, a number of light spots of various colors created by spectral dispersion are observed around this pattern. In addition, these spots create a regular pattern.

On the other hand, the photograph of FIG. 23(B) was taken from a diamond which was cut roughly and had poor proportions. Although this diamond should be identical in carat and diameter with the diamond of FIG. 23(A), the diameter of the resulting image is smaller than that of FIG. 23(A). Additionally, the contour is greatly uneven, which forms a contrast with the photograph of FIG. 23(A) where the contour is substantially circular. Furthermore, the image of FIG. 23(A) is darker as a whole than the image of FIG. 23(A). Moreover, the number of the light spots and the kinds of colors are fewer. Further, the pattern of the diamond of this photograph has no regularity as a whole. An arrow-shaped pattern such as seen on the photograph of FIG. 23(A) does not appear at all.

In this way, the novel photography method enables one to photograph a pattern consisting of various colors attributed to the brilliance specific to the diamond and created by spectral dispersion. The degree of brilliance reflecting the quality of the cutting of the diamond and the proportions, the colors of the brilliance created by spectral dispersion, and the distribution of bright spots can be easily known from the pattern.

Figure 24A:
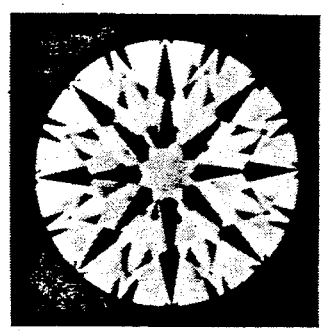
FIGS. 24(A) and 24(B) are photographs of diamonds taken by the prior art method.
Figure 24B:
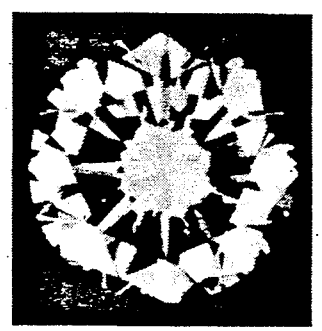

For comparison, photographs of diamonds used in conventional written statement of an expert opinion on gems are shown in FIGS. 24(A) and 24(B). The photograph of FIG. 24(A) shows a well cut diamond, while the photograph of FIG. 24(B) shows a poorly cut diamond. To take each of these photographs, the gem was placed between a black board and a reflecting plate having a hole extending through it. Light was made to hit the gem from obliquely below. The photograph was taken from above by a camera through the hole in the reflecting plate.

In this method of photography, it is totally impossible to catch a pattern consisting of various colors produced by spectral dispersion in the diamond. In particular, if a color picture is taken, the pattern on the photograph only shows lights and shades of colors. Various colors which are successfully detected by the novel method can by no means be caught. Therefore, in these photographs, it is totally impossible to know the colors of light producing the brilliance specific to diamonds or the number of the colors.

Also, in these photographs, those portions which are brightest and least bright to the naked eye are black. The remaining portions are whitish. Although arrow-shaped patterns appear in these photographs, the arrow which should be brightest appears black. For this reason, it is impossible for ordinary persons to visually sense the correspondence to the brilliance of the diamonds. In addition, it is wholly impossible to distinguish between the brightest portions and the least bright portions, because the latter portions appear black. For example, in the photograph of FIG. 24(B), black portions exist between the center and the outer fringes, i.e., in the intermediate portions. It is utterly impossible to know whether these portions are brightest or least bright. The portions other than black portions are generally whitish and have almost no shades. As can be seen from the photography of FIG. 23, these portions should have various degrees of brilliance. However, it is almost impossible to distinguish them from each other. Accordingly, the general impression is that almost no three-dimensionality exits.

Figure 25A:
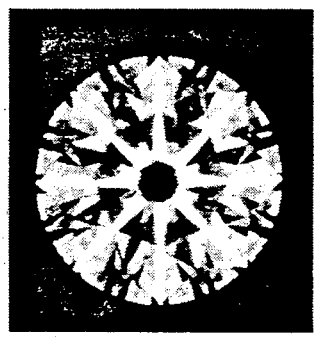
FIGS. 25(A) and 25(B) are photographs of diamonds taken by the method previously proposed by the present inventor.
Figure 25B:
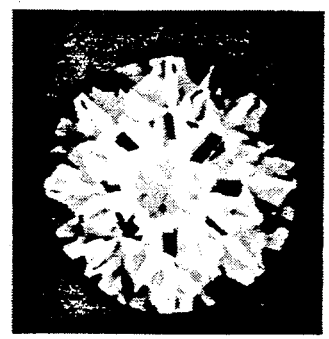

For comparison, photographs taken by the method already proposed by the present applicant in Japanese Patent Application No. 32399/1990 are shown in FIGS. 25(A) and 25(B). Each of these photographs was taken by placing a diamond at the bottom of an implement consisting of a layer cylindrical portion of given dimensions and a upper cylindrical portion made of a semi-transparent material and then taking a picture of the diamond through an opening formed at the top of the implement.

The fringes in these photographs which are affected by the amount of reflection occurring inside the diamonds have more varied colors than the fringes in the photographs shown in FIG. 24 and taken by the prior art method. In addition, the brightest portions appear white. The less bright portions have the deeper colors. Also, the correspondence between the actual brilliance and the shades of the fringes is good. However, even in this method, the colors of the photographed fringes consist of only white and one color having shades. Furthermore, it is not the case that varied colors are created by the brilliance specific to diamond, unlike in the novel method.

What is claimed is:

1. A method of observing or photographing a gem such as a diamond, comprising the steps of:

placing the gem inside a container having an opening at the top in such a way that light can enter the container from directions lying within the range of angles of 20 to 50 degrees about the line vertical to the gem; and observing or photographing the gem from above while directing light into the container from above.

2. A method of observing or photographing a gem as set forth in claim 1, further comprising the step of placing a reflecting plate having a hole in its center above the container such that light coming from below is reflected into the container by the reflecting plate, and wherein said step of observing or photographing the gem from above while directing light into the container from above is carried out through the hole in the reflecting plate.

3. A method of observing or photographing a gem as set forth in claim 2, wherein said reflecting plate has a specular reflecting surface.

4. A method of observing or photographing a gem as set forth in claim 3, wherein said reflecting plate has a reflecting surface consisting of a plurality of small specular surfaces surrounding said hole, and wherein the small specular surfaces are so oriented that light coming from below is reflected into the container by these small specular surfaces.

5. A method of observing or photographing a gem as set forth in claim 2, wherein said reflecting plate has a reflecting surface that is white or light in color.

6. A method of observing or photographing a gem as set forth in claim 2, wherein said reflecting plate has a reflecting surface made of a glossy metal surface.

7. A method of observing or photographing a gem as set forth in claim 6, wherein said reflecting plate has a reflecting surface made of an uneven metal surface.

8. A method of observing or photographing a gem as set forth in any one of claim 2, 3, 4, 5, 6, and 7, wherein either the container of the opening in the container is surrounded by a surface that is white or light in color, and wherein the light reflected by this surface is directed to the overlying reflecting plate.

9. A method of observing or photographing a gem as set forth in any one of claims 2, 3, 4, 5, 6, and 7, wherein either the container or the opening in the container is surrounded by a specular surface or glossy metal surface, and wherein the light reflected by this surface is directed to the overlying reflecting plate.

10. A method of observing or photographing a gem as set forth in any one of claim 2, 3, 4, 5, 6, and 7, wherein an illuminating device is disposed above the container such that the light emitted by this illuminating device is directed to the vicinities of the container or to the vicinities of the opening in the container, and wherein the light reflected by these vicinities is directed to the overlying reflecting plate.

11. A method of observing or photographing a gem as set forth in any one of claims 2, 3, 4, 5, 6, and 7, wherein
(A) either the container or the opening in the container is surrounded by a white or light-colored surface,
(B) an illuminating device is disposed above the container such that the light emitted by this illuminating device is directed to the vicinities of the container or to the vicinities of the opening in the container, and
(C) the light reflected by these vicinities is directed to the overlying reflecting plate.

12. A method of observing or photographing a gem as set forth in any one of claims 2, 3, 4, 5, 6, and 7, wherein
(A) either the container or the opening in the container is surrounded by a specular surface or glossy metal surface,
(B) an illuminating device is disposed above the container such that the light emitted by this illuminating device is directed to the vicinities of the container or to the vicinities of the opening in the container, and
(C) the light reflected by these vicinities is directed to the overlying reflecting plate.

13. A method of observing or photographing a gem as set forth in any one of claims 2, 3, 4, 5, 6, and 7, wherein an illuminating device is disposed either around the container or around the opening in the container, and wherein the light emitted by this illuminating device is directed to the overlying reflecting plate.

14. A method of observing or photographing a gem as set forth in claim 1, wherein an illuminating device is disposed above the container, and wherein the light emitted by the illuminating device is directed into the container.

15. An implement used for observation or photography as set forth in claim 1, comprising:
a container having an opening at the top:
a reflecting plate having a hole in its center and disposed above the container such that the light reflected by this reflecting plate enters the container;
a seat portion on which a gem is placed, the seat portion being located substantially in the center of the bottom of the container;
and wherein the straight lines connecting the seat portion with the opposite fringes, respectively, of the opening form an angle of 20 to 50 degrees with each other.

16. An implement used for observation or photography as set forth in claim 1, comprising:
a container having an opening at the top;
a reflecting plate having a hole in its center and disposed above the container such that the light reflected by this reflecting plate enters the container;
an illuminating device for directing light to a surface facing upward around the container or around the opening in the container;
a seat portion on which a gem is placed, the seat portion being located substantially in the center of the bottom of the container;
and wherein the straight lines connecting the seat portion with the opposite fringes, respectively, of the opening form an angle of 20 to 50 degrees with each other.

17. An implement used for observation or photography as set forth in claim 1, comprising:
a container having an opening at the top;
a reflecting plate having a hole in its center and disposed above the container such that the light reflected by this reflecting plate enters the container;
an illuminating device disposed either around the container or around the opening in the container for directing light to the reflecting plate;
a seat portion on which a gem is placed, the seat portion being located substantially in the center of the bottom of the container;
and wherein the straight lines connecting the seat portion with the opposite fringes, respectively, of the opening form an angle of 20 to 50 degrees with each other.

18. The implement of claim 15, 16, or 17, wherein the reflecting surface of the reflecting plate located above the container is specular.

19. The implement of claim 18, wherein the reflecting surface consists of a number of small specular surfaces which are so oriented that light coming from around the container is reflected into the container by the small specular surfaces.

20. The implement of claim 15, 16, or 17, wherein the reflecting surface of the reflecting plate located above the container is white or light in color.

21. The implement of claim 15, 16, or 17, wherein the reflecting surface of the reflecting plate located above the container is a glossy metal surface.

22. The implement of claim 21, wherein the metal surface forming the reflecting surface is uneven.

23. The implement of claim 15 or 16, wherein either the container or the opening in the container is surrounded by a surface that is white or light in color.

24. The implement of claim 15 or 16, wherein the reflecting surface of the reflecting plate located above the container is specular, and wherein either the container or the opening in the container is surrounded by a surface that is white or light in color.

25. The implement of claim 15 or 16, wherein the reflecting surface of the reflecting plate located above the container is white or light in color, and wherein either the container or the opening in the container is surrounded by a surface that is white or light in color.

26. The implement of claim 15 or 16, wherein the reflecting surface of the reflecting plate located above the container is a glossy metal surface, and wherein either the container or the opening in the container is surrounded by a surface that is white or light in color.

27. The implement of claim 15 or 16, wherein either the container or the opening in the container is surrounded by a specular surface or glossy metal surface.

28. The implement of claim 15 or 16, wherein the reflecting surface of the reflecting plate located above the container is specular, and wherein either the container or the opening in the container is surrounded by a specular surface or glossy metal surface.

29. The implement of claim 15 or 16, wherein the reflecting surface of the reflecting plate located above the container is white or light in color, and wherein either the container or the opening in the container is surrounded by a specular surface or glossy metal surface.

30. The implement of claim 15 or 16, wherein the reflecting surface of the reflecting plate located above the container is a glossy metal surface, and wherein either the container or the opening in the container is surrounded by a specular surface or glossy metal surface.

31. The implement of claim 15 or 16, wherein the reflecting surface located above the container consists of a number of small specular surfaces which are so oriented that light coming from around the container is reflected into the container by the small specular surfaces, and wherein either the container or the opening in the container is surrounded by a surface that is white or light in color.

32. The implement of claim 15 or 16, wherein the reflecting surface of the reflecting plate located above the container consists of a number of small specular surfaces which are so oriented that light coming from around the container is reflected into the container by the small specular surfaces, and wherein either the container or the opening in the container is surrounded by a surface that is a specular surface or glossy metal surface.

33. The implement of claim 15 or 16, wherein the reflecting surface of the reflecting plate located above the container is an uneven and glossy metal surface, and wherein either the container or the opening in the container is surrounded by a surface that is white or light in color.

34. The implement of claim 15 or 16, wherein the reflecting surface of the reflecting plate located above the container is an uneven and glossy metal surface, and wherein either the container or the opening in the container is surrounded by a surface that is a specular surface or glossy metal surface.

35. An implement used for observation or photography as set forth in claim 1, comprising:
 a container having an opening at the top;
 an illuminating device disposed above the container such that the light emitted by the illuminating device enters the container;
 a seat portion which is formed substantially in the center of the bottom of the container and on which a gem is placed;
 and wherein the straight lines connecting the seat portion with the opposite fringes, respectively, of the opening form an angle of 20 to 50 degrees with each other.

36. The implement of claim 35, wherein the illuminating device consists of a holder having a hole in its center and a plurality of illuminators mounted to the underside of the holder so as to surround the hole.

37. The implement of claim 35, wherein the illuminating device consists of a holder having a hole in its center and an annular illuminator mounted to the underside of the holder so as to surround the hole.

* * * * *